US011648258B2

(12) United States Patent
Liang et al.

(10) Patent No.: US 11,648,258 B2
(45) Date of Patent: May 16, 2023

(54) METHOD AND COMPOUNDS FOR INHIBITING THE MCM COMPLEX AND THEIR APPLICATION IN CANCER TREATMENT

(71) Applicants: The Hong Kong University Of Science And Technology, Kowloon (CN); Hong Kong Baptist University, Kowloon (CN); Macau University Of Science And Technology, Macao (CN)

(72) Inventors: Chun Liang, N.T. (HK); Zhihong Jiang, Macao (CN); Ziyi Wang, N.T. (HK); Zhiling Yu, N.T. (HK); Jingrong Wang, Macao (CN); Liping Bai, Macao (CN)

(73) Assignees: The Hong Kong University Of Science And Technology, Kowloon (CN); Hong Kong Baptist University, Kowloon (CN); Macau University Of Science And Technology, Macao (CN)

( * ) Notice: Subject to any disclaimer, the term of this patent is extended or adjusted under 35 U.S.C. 154(b) by 573 days.

(21) Appl. No.: 14/399,960

(22) PCT Filed: May 9, 2013

(86) PCT No.: PCT/US2013/040287
§ 371 (c)(1),
(2) Date: Nov. 9, 2014

(87) PCT Pub. No.: WO2013/169989
PCT Pub. Date: Nov. 14, 2013

(65) Prior Publication Data
US 2015/0099712 A1    Apr. 9, 2015

Related U.S. Application Data

(60) Provisional application No. 61/644,442, filed on May 9, 2012.

(51) Int. Cl.
*A61K 31/7048* (2006.01)
*A61K 31/585* (2006.01)
*G01N 33/50* (2006.01)
*G01N 33/574* (2006.01)

(52) U.S. Cl.
CPC ........ *A61K 31/7048* (2013.01); *A61K 31/585* (2013.01); *G01N 33/5011* (2013.01); *G01N 33/5044* (2013.01); *G01N 33/574* (2013.01); *G01N 2458/00* (2013.01); *G01N 2500/10* (2013.01)

(58) Field of Classification Search
CPC ................. A61K 31/7028–7048; C07H 15/24
See application file for complete search history.

(56) References Cited

U.S. PATENT DOCUMENTS

| 7,393,950 B2 | 7/2008 | Liang et al. |
| 8,318,922 B2 | 11/2012 | Liang et al. |
| 2009/0018088 A1* | 1/2009 | Valdes, Jr. ............ A61K 31/704 514/26 |
| 2011/0311651 A1 | 12/2011 | Djaballah et al. |

FOREIGN PATENT DOCUMENTS

| CN | 101683359 A | 3/2010 |
| CN | 102219821 A | 10/2011 |
| JP | H0592990 A | 4/1993 |
| JP | 2004131435 A | 4/2004 |
| JP | 2006514545 A | 5/2006 |
| JP | 2008525479 A | 7/2008 |
| JP | 2009515932 A | 4/2009 |
| WO | 0214343 A1 | 2/2002 |
| WO | 2005099747 A1 | 10/2005 |

OTHER PUBLICATIONS

Cheenpracha, S. et al "New cytotoxic cardenolide glycoside . . . " Chem. Pharm. Bull. (2004) vol. 52, No. 8, pp. 1023-1025.*
Chemical Abstracts entry for 17beta-neriifolin and 17alpha-neriifolin. (Year: 2021).*
Chemical Abstracts entry for Valdes US 2009/0018088. (Year: 2009).*
Jolad, S. et al "3'-O-Methylevomonoside . . . " J. Org. Chem., vol. 46, pp. 1946-1947. (Year: 1981).*
Prassas, I. et al "Novel therapeutic applications of cardiac glycosides" Nature Rev., Drug Disc., vol. 7, pp. 926-935. (Year: 2008).*
El Tanbouly, N. et al "Cytotoxic cardiac glycosides . . . " Bull. Fac. Pharm. Cairo Univ., vol. 38, No. 3, pp. 103-105. (Year: 2000).*
Decosterd, L. et al "The differntial cytotoxicity of cardenolides . . . " Phytother. Res., vol. 8, pp. 74-77. (Year: 1994).*
Miyagawa, T. et al "Cardenolide glycosides of Thevetia peruviana . . . " J. Nat. Prod., vo 72, pp. 1507-1511. (Year: 2009).*
Sarot Cheenpracha, et al., Chem. Pharm. Bull., 2004, pp. 1023-1025, vol. 52, No. 8.
Ching-Han Yu, et al., Cancer Sci, 2008, pp. 2467-2476, vol. 99, No. 12.
Rui-Fang Xie, et al., Journal of Ethnopharmacology, 2012, pp. 692-700, vol. 141.
Hiroshi Kimura, et al., Genes to Cells, 1996, pp. 977-993, vol. 1.
Xiao-Hui Zhang, et al., Chemistry and Biodiversity, 2007, pp. 998-1002, vol. 4.
Raymond W. Doskotch, et al., Journal of Pharmaceutical Sciences, 1972, pp. 570-573, vol. 61, No. 4.
Hao-Fu Dai, et al., Molecules, 2009, pp. 3694-3699, vol. 14.
Shirin Karimi, et al., DNA Replication and Related Cellular Processes, 2011, pp. 1-14.

(Continued)

*Primary Examiner* — Leigh C Maier
(74) *Attorney, Agent, or Firm* — Bayramoglu Law Offices LLC

(57) ABSTRACT

A method for treating cancer by using an agent which is capable of inhibiting the functionality of the MCM complex, a heterohexameric ring formed from six subunits, in the process of DNA replication and a method of screening for such agents by detecting the locations and functions of the MCM subunits, such as hMcm2 and hMcm6, in cells treated with candidate compounds.

8 Claims, 15 Drawing Sheets

(56) References Cited

OTHER PUBLICATIONS

Gouji Toyokawa, et al., Molecular Cancer, 2011, pp. 1-11, 10:65.
Li-Ru Shen, et al., Chemistry & Biodiversity, 2007, pp. 1438-1449, vol. 4.
Lei Ming, Current Cancer Drug Targets, 2005, vol. 5, No. 5.
Rentian Wu, et al., Journal of Cell Science, 2012, pp. 209-219, vol. 125, No. 1.
K-M Lau, et al., Oncogene, 2010, pp. 5475-5489, vol. 29.
Xu Yan, et al., Journal of Guangxi Academy of Sciences, 2011, pp. 55-61, vol. 27, No. 1.
Jojo VV, et al., Journal of the Indian Society of Toxicology (Jist), 2007, pp. 22-26, vol. 3 Issue 001.
Qian Zhao, et al., Fitoterapia, 2011, pp. 735-741, vol. 82.
Shahana Majid, et al., Cancer Research, 2010, pp. 2809-2818, vol. 70, No. 7.

* cited by examiner

METHOD AND COMPOUNDS FOR INHIBITING THE MCM COMPLEX AND THEIR APPLICATION IN CANCER TREATMENT

CROSS-REFERENCE TO RELATED APPLICATION

This application claims benefit from U.S. provisional application No. 61/644,442, filed May 9, 2012, the content of which is incorporated herein by reference in its entirety.

FIELD OF THE INVENTION

This invention relates to a method for treating cancer by using an agent which is capable of inhibiting the functionality of the MCM complex, a heterohexameric ring formed from six subunits, in the process of DNA replication, and it further relates to a method of screening for such agents by detecting the locations and functions of the MCM subunits, such as hMcm2 and hMcm6, in cells treated with candidate compounds.

BACKGROUND OF THE INVENTION

Cancerous cells are cells that divide and grow uncontrollably, invade nearby parts of the body, and may also spread to other parts of the body through the lymphatic system and/or bloodstream. Cancer treatment usually involves removal or destruction of cancerous cells, such as, by surgery, chemotherapy, radiation therapy, or immunotherapy, etc. However, one of the challenges in all those forms of treatment is how to completely remove or destroy the cancerous cells and at the same time cause no serious damages to normal or healthy cells and tissues. In case of chemotherapy, for several decades, screening for cytotoxic compounds had been the major focus of the research and development afford. A great number of chemical compounds have been indicated to have cytotoxic and anticancer activities. As noted by Schwartsmann et al., by 1988, over 600,000 compounds have been screened but only around 40 of them are of any clinical significance. This low success rate is largely due to toxicity concerns for anticancer drugs, which generally have a narrow therapeutic index, that is, having a small margin between the dose required for an anticancer effect and that causing unacceptable toxicity. The usefulness of discovering compounds that have inhibitory effects on cell proliferation based on cytotoxicity is limited and it is far away of being clinically relevant. What is needed and more meaningful is to find compounds that not only potently inhibit cell proliferation but also do so with specificity towards cancerous cells, without causing serious damages to normal or healthy cells and tissues.

SUMMARY OF THE INVENTION

Accordingly, one object of the present invention is to provide a method of destroying cancerous cells with high specificity without causing significant damages to normal cells. This object is realized by a means of disrupting the formation of functional MCM (minichromosome maintenance) complex from its subunits. It is known that the MCM complex plays an essential role in pre-RC (i.e., pre-replicative complex) assembly, which is also referred to as replication licensing, and DNA replication elongation. Functional MCM complex requires all six MCM subunits (Mcm2-7) to form a heterohexameric ring, which is loaded onto replication origin with the help of Orc1-6, Noc3, Ipi1-3, Cdt1, Cdc6 and perhaps some other proteins. As a member of the AAA+ (ATPases associated with a variety of activities) family of proteins, the MCM complex moves along with the replication fork, likely to serve as the replicative helicase to unwind the DNA double strands. The inventors' previous research, disclosed in the U.S. Pat. Nos. 7,393,950 and 8,318,922, has demonstrated that antisense oligonucleotides targeting genes of MCM subunits have the effect of inhibiting cell proliferation. The contents of the aforementioned patents are incorporated herewith by reference.

Because the MCM proteins must form an intact complex with a ring structure in order to be functional, disruption of their interactions (i.e., making them unable to form a functional complex) will inhibit DNA replication and induce apoptosis and, more importantly, the effect of disrupting MCM's functionality is only serious and permanent on cancerous cells, and not on normal and healthy cells.

Such a high specificity is the essence of the present invention. While not wishing to be bound by theory, it is believed that the high specificity of the present invention lies in the difference that normal cells possess intact checkpoints which arrest the cell cycle in G1 phase to avoid cell death, whereas cancer cells lack checkpoint controls and will enter into an abortive S phase. In other words, normal cells have the ability to sense whether the MCM complex has been formed and functional and only enter into the S phase when they know that the MCM complex is ready to play its rules in the DNA replication. Otherwise they will be temporarily arrested in G1 phase. To use an analogy, this is like a running vehicle equipped with a functioning break. It can be stopped once the driver realizes that the bridge over the river ahead is broken. On the other hand, the cancerous cell is like a vehicle having a dysfunctional break and it cannot stop before reaching the broken bridge and will continue its course until falling into the river (that is, running into abortive S phase).

Another object of the present invention is to provide a method of screening for anticancer drugs with high specificity which destroy cancerous cells while not causing serious damages to normal cells. This object is realized by a process to identify compounds that impair the formation of the functional MCM complex (a heterohexameric ring structure) from subunits, which will remain in the cytoplasm and cannot be transported to the nucleus.

Preferably, the method comprises steps of (a) contacting a number of candidate compounds with a population of cells for a period of time and (b) detecting the level of functional MCM complex in the cells treated with the candidate compounds. More preferably, step (b) is performed indirectly by detecting the portion of the MCM subunits located in the nucleus as compared with the portion located in the cytoplasm. Because only the functional MCM complex can be located within the nucleus, the less MCM subunits are located in the nucleus, the more potent the candidate compound's disruptive effect on the formation of functional MCM complex is. Still more preferably, step (b) is performed by an indirect fluorescence method (immunostaining) where fluorescently labeled secondary antibodies that recognize the primary antibodies against one or more endogenous MCM proteins allow visualization of the sub-cellular locations of the endogenous MCM proteins after being exposed to the candidate compounds for a certain duration. Alternatively, step (b) may also be performed by a direct fluorescence method where the cells have been transfected with plasmids capable of expressing one or more MCM subunits fused with a fluorescent protein, such as, for example, hMcm2-GFP and/or hMcm6-GFP, whereby the locations of the fluorescent MCM fusion proteins after the cells being treated with the candidate compounds can be detected. Other methods for step (b) include detecting the physical interactions of the MCM subunits, or to measure the amount of MCM proteins bound on chromatin where MCM proteins normally perform their functions.

Optionally, additional steps may be performed to supplement step (b) or as a separate step to examine DNA replication defects by methods such as BrdU incorporation assay, flow cytometry, etc. Further steps may also been taken to confirm that compounds identified with the ability to disrupt the formation of functional MCM complex are also having potent differential effects in terms of anti-proliferation and inducing apoptosis between cancerous cells and normal cells.

Another object of the present invention is to provide specific compounds as anticancer agents with high specificity to embody the therapeutic method according to the present invention.

The method and compounds of the present invention is applicable to all forms of cancer sensitive to disruption of the MCM complex, for example, cervical cancer, prostate cancer, colon cancer, breast cancer, ovary cancer, acute myelocytic leukemia, chronic lymphocytic leukemia, Non-Hodgkin's disease lymphoma, Hodgkin's disease lymphoma, acute lymphocytic leukemia, pancreatic cancer, stomach cancer, skin cancer, bladder cancer, esophageal cancer, nasopharyngeal carcinoma, small cell lung cancer, follicular lymphoma, or non-small cell lung cancer.

In sum, the special technical feature underlying the present invention involves an agent capable of selectively destroying cancerous cells by interrupting the formation of functional MCM complex from its subunits.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

Cell Lines and Plasmids

Figure 1:
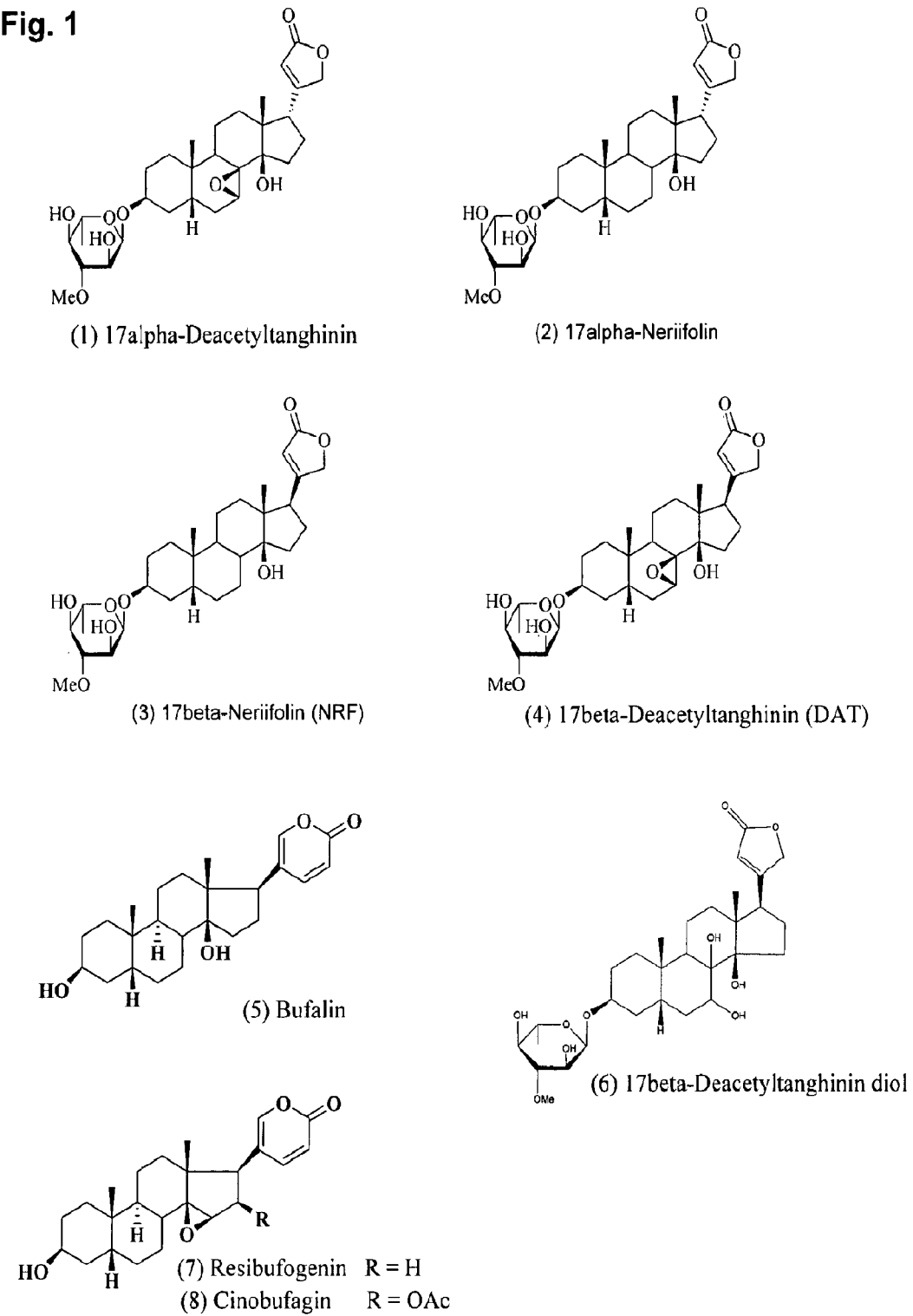
FIG. 1 shows the structures of anticancer compounds (3-8) of the present invention in comparison with that of inactive isomers (1-2).

Human Mcm6 and Mcm2 cDNA fragments were each cloned into the pEGFP-C3 vector (Invitrogen) for localization detection. HeLa cells (cervical adenocarcinoma), HepG2 cells (hepatocellular carcinoma), Hep3B cells (hepatocellular carcinoma), HK1 (nasopharyngeal carcinoma), and C666-1 (nasopharyngeal carcinoma) were cultured in DMEM containing 10% of FBS. L-02 cells (normal human liver cells) were cultured in RPMI 1640 with 10% FBS. NP460 cells were cultured in 1:1 Keratinocyte-SFM (Invitrogen) and MEPI 500CA with supplement S0125 (Cascade Biologics). All cell lines were cultured at 37° C. in a humidified atmosphere containing 5% of $CO_2$.

Anti-Proliferation Activity Assay

For testing the anti-proliferation activity of the compounds in human cell lines and calculation of $IC_{50}$, cancer cells including HepG2, HeLa and Hep3B ($4\times10^5$ cells/well) and normal L-02 cells ($5\times10^5$ cells/well) were respectively seeded in 96-well plates in 100 μl of culture medium and incubated for about 12 hrs at 37° C. The cells were treated with two-fold serial dilutions of the drugs for 48 hrs. Medium was removed and 100 μl of culture medium containing 1 μM WST-1 (water soluble tetrazolium-1) were added to each well. The cells were incubated for 2 hrs, and absorbance at 405 nm (reference at 630 nm) was then measured. To construct the standard curve of the relationship between cell number and absorbance at $OD_{405}$, serial dilutions of cells with known cell numbers were seeded and incubated for six hrs before being measured by the WST-1 assay. The cell viability was expressed as the ratio of the number of live cells treated with a candidate compound versus that of the DMSO-treated cells.

Natural Product Screening and Bioactivity-Guided Isolation of Anticancer Compounds A general protocol for preparing chemical samples from natural source for the anticancer drug screen assay was as follows: 10-100 grams of the herb material (whole plant, root, stem, leave or fruit) were extracted with methanol at room temperature three times. Each total extract was suspended in water and then partitioned with $Et_2O$, EtOAc, n-BuOH successively, to afford four fractions, i.e. $Et_2O$ fraction, EtOAc fraction, n-BuOH fraction and $H_2O$ fraction. Each total extract or fraction was dissolved in DMSO as a 10 mg/ml stock for the screening assay. Purified single compounds were prepared as 1 mg/ml stock each.

Using the above screening approach, one fraction was identified with potent MCM complex-disrupting and anticancer activities, which is the $Et_2O$ fraction of the extract of dried leaves or young braches of *Cerebra manhas* and *Cerebra odollam*. This fraction was subsequently subjected to activity-guided fractionation by using a combination of different column chromatography over $SiO_2$, MCI-gel CHP 20P (75-150m, Mitsubishi Chemical Corporation, Japan), Chromatorex ODS (100-200 mesh, Fuji Silysia Chemical Ltd., Japan) and Toyopearl HW-40F (Tosoh Corporation, Japan), resulting in the isolation of 17beta-Deacetyltanghinin as a lead compound responsible for the activity of the active fraction of dried leaves and young braches of *Cerebra odollam* and *Cerebra manhas*.

Structure Identification of 17Beta-Deacetyltanghinin

Structure of 17beta-Deacetyltanghinin was characterized on the basis of spectroscopic evidence. NMR spectra were recorded using a Varian-400 spectrometer. Coupling constants were given in Hz and chemical shifts were represented in (ppm) relative to Me4Si as the internal standard. HR-ESI-MS was preformed on a Q-TOF mass spectrometer (Bruker Daltonics, MA, U.S.A).

High Resolution-ESI-MS (Positive ion mode): m/z 549.3077 $[M+H]^+$ (calculated for $C_{30}H_{45}O_9$: 549.3064). $^1$H-NMR (400 MHz, pyridine-d5): δ 6.31 (1H, s, H-22), 5.25 (1H, d, J=2.9 Hz, H-1'), 5.20 (1H, m, H-21), 5.02 (1H, dd, J=18.0, 1.4 Hz, H-21), 4.33 (1H, m, H-5'), 4.12 (1H, brs, H-3), 4.09 (1H, dd, J=9.0, 4.0 Hz, H-2'), 4.03 (1H, t, J=9.5 Hz, H-3'), 3.85 (3H, s, 3'-OMe), 3.69 (1H, m, H-4'), 3.41 (1H, d, J=5.8 Hz, H-7), 2.82 (1H, dd, J=9.0, 5.0 Hz, H-17), 1.66 (1H, d, J=6.2 Hz, H-6'), 1.06 (3H, s, H-19), 0.99 (3H, s, H-18). $^{13}$C-NMR (100 MHz, pyridine-d5): (532.7 (C-1), 28.0 (C-2), 73.7 (C-3), 33.5 (C-4), 34.8 (C-5), 28.9 (C-6), 51.9 (C-7), 65.1 (C-8), 32.5 (C-9), 34.4 (C-10), 21.5 (C-11), 41.4 (C-12), 53.2 (C-13), 82.4 (C-14), 35.9 (C-15), 29.3 (C-16), 51.5 (C-17), 13.0 (C-18), 25.0 (C-19), 175.9 (C-20), 74.4 (C-21), 113.4 (C-22), 175.1 (C-23), 99.6 (C-1'), 74.0 (C-2'), 86.0 (C-3'), 77.2 (C-4'), 69.6 (C-5'), 19.2 (C-6'), 61.2 (C-3'-OMe).

17beta-Deacetyltanghinin was determined to be a cardenolide monoglycoside by its high resolution ESI-MS which corresponds to a molecular formula of $C_{30}H_{44}O_9$, the $^1$-NMR spectra which show characteristic signals arising from cardenolide [methylene proton at C-21 (δ 5.20, m; 5.02, dd, J=18.0, 1.4 Hz) and olefinic proton at C-22 (δ 6.31, s)], and the signals of anomeric proton (δ 5.25, d, J=2.9 Hz) of the sugar moiety. An epoxy group at C-7 and C-8 positions was suggested by the large downfield shift for the C-7 and C-8 signals compared to those of nerriforlin, a major cardenolide from the leaves of *Cerbera manghas*, and further supported by chemical shift comparison with those of cardenolides possessing a 7,8-epoxy group. The configuration of C-17 was established to be β as evidenced by the signal of H-17 (δ 2.82, dd, J=9.0, 5.0 Hz) and supported by the signal of C-12 (b, 41.4) which is under the shielding effect of the lactone ring. The aglycone was identified as 3β-hydroxy-7β,8β-epoxy-14β-hydroxy-card-20(22)-enolide by comparing its $^{13}$C-NMR data with those reported. The sugar moiety was revealed to be α-L-thevetose (3-O-methyl-6-deoxy-α-L-glucopyranosyl) by comparison of its proton and the carbon signals with those described in the literature. Based on the above evidence, the structure of HMG-17beta-Deacetyltanghinin was characterized to be 3β-O-(3-O-methyl-6-deoxy-α-L-glucopyranosyl)-7β,8β-epoxy-14β-hydroxy-card-20(22)-enolide (17beta-Deacetyltanghinin):

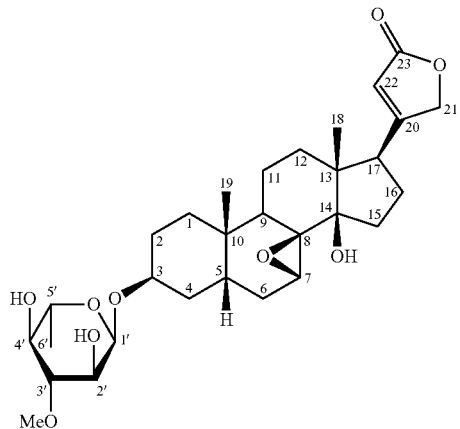

Immunostaining Assay

To study the effect of the anticancer compounds on the interaction between hMcm2 and hMcm6 in the cells, immunostaining was performed to detect the sub-cellular localization of the proteins. HeLa cells grown on cover slips (coated with poly-D-lysine) with or without drug treatment were fixed with 4% PFA in PBS at room temperature for 20 min. After permeabilization with 0.1% Triton X-100 and 1% BSA in PBS for 20 min, cells were blocked with 1% BSA and then incubated with rabbit anti-hMcm6 (Santa Cruz; 1:500) and mouse anti-hMcm2 (Becton Dickinson; 1:500) primary antibodies at room temperature for 1 hr. Cells were then incubated with Alexa Fluor 488-conjugated donkey anti-goat antibody and Alexa Fluor 594-conjugated donkey anti-mouse antibody (Invitrogen; 1:500) at room temperature for 1 hr. Three washes with PBS were performed after each round of antibody incubation. Cells were then incubated with Hochest 33852 (Sigma Chemical Company; 1 μg/ml) at room temperature for 15 min for nuclear staining and washed with PBS three times again. At last, cells were mounted and observed under the fluorescence microscope (Nikon TE2000E).

Cell Synchronization

To arrest cells in M phase, HeLa cells were pre-synchronized with 2 μM thymidine for 18 hrs, released into fresh medium for 6 hrs, and then arrested in early M phase with 0.1 μg/ml nocodozole for 6 hrs. HeLa cells were arrested at the G1/S phase boundary by treatment with 0.5 mM mimosine for 20 hrs. An aliquot of G1/S phase cells were then released into hydroxyurea-containing medium for 4 hrs to obtain early S phase cells.

BrdU Incorporation Assay

Hela cells grown on cover slips coated with poly-D-lysine were incubated with 50 μM BrdU (Sigma) for 1 hr at 37° C. after 24 hrs of 17beta-Deacetyltanghinin treatment. Cells were then fixed in with 4% of PFA in PBS at room temperature for 20 min, permeabilized with 0.1% Triton X-100 and 1% BSA in PBS for 20 min, and then incubated sequentially with anti-BrdU (Sigma Chemical Company; 1:500) and anti-mouse IgG-FITC conjugates (Sigma Chemical Company; 1:500), each for 1 hr at 37° C., with three washes in PBS after each antibody incubation. BrdU signal was observed under the fluorescence microscope (Nikon TE2000E).

Chromatin Binding Assay

Cells were harvested by trypsinization and washed twice with cold PBS. Extraction buffer (EB; ~20 μl/$10^6$ cells) (100 mM KCl, 50 mM HEPES-KOH pH7.5, 2.5 mM $MgCl_2$, 50 mM NaF, 5 mM $Na_4P_2O_7$, 0.1 mM $NaVO_3$, 0.5% Triton X-100, 1 mM PMSF, 2 μg/ml Pepstatin A, 20 μg/ml Leupeptin, 20 μg/ml Aprotinin, 0.2 mM Pefabloc, 2 mM Benzamidine HCl and 0.2 mg/ml Bacitracin) was added to resuspend and lyse the cells by pippetting. Cells were set on ice for 10 min, and flicked to mix every 2-3 min during the incubation. A volume of 30% ice-cold sucrose equal to EB containing protease inhibitors as in EB was added to the bottom of tube. The tube was spun at top speed in a microcentrifuge for 10 min to separate the chromatin and free proteins. The supernatant was transferred to a new tube and kept on ice. The pellet was washed with equal volume of EB by flicking the tube to dislodge the pellet from the wall of the tube and resuspended by brief vortexing. The suspension was spun again at top speed for 5 min. The two supernatants were combined. The pellet was resuspended in EB equal to half volume of the supernatant. The supernatant and pellet fractions were finally treated for immunoblotting.

Flow Cytometry (FACS Analysis)

Both floating and attached cells were collected and washed once with PBS. Cells were fixed in 70% ethanol for 1 hr to overnight at −20° C., washed thoroughly with PBS, and then stained in 50 μg/ml RNase A, 0.1% Triton X-100, 0.1 mM EDTA (pH 7.4), and 50 μg/ml propidium iodide for 30 min at 4° C. Samples were analyzed with the FACSort instrument (Becton Dickinson).

towards normal cells. In FIG. 2B-H, quantification of viable cell numbers was carried out using WST-1 (Water-soluble tetrazolium-1) assay.

Figure 2A:
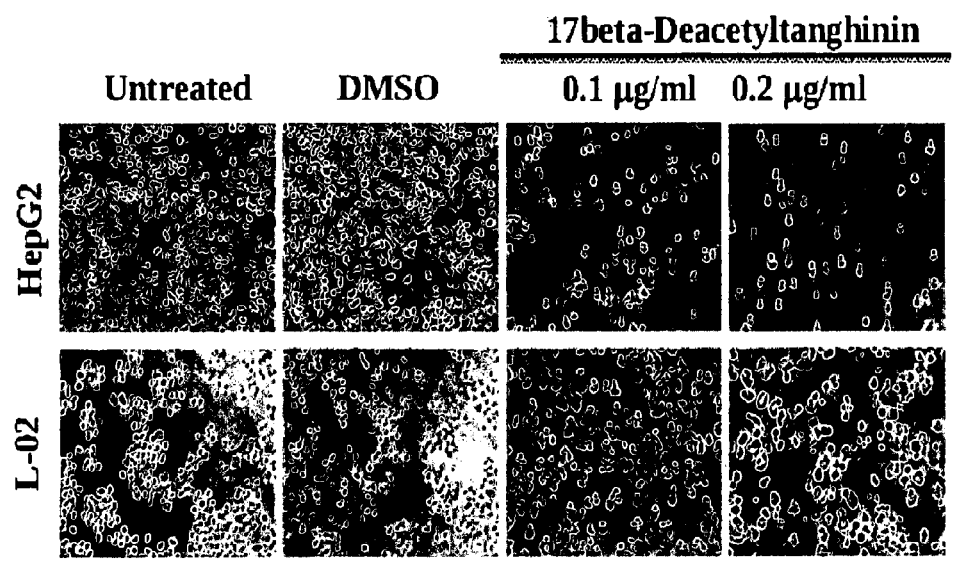
FIG. 2 presents direct microscopy observation (A) and WST-1 (water soluble tetrazolium-1) assay data (B-H), showing that 17beta-Deacetyltanghinin (A-C), 17beta-Neriifolin (D) and 17beta-Deacetyltanghinin diol (E), three representatives of the anticancer compounds of the present invention, have strong anti-cancer activities without significant cytotoxicity towards normal cells. For comparison, Paclitaxel (Taxol) is more cytotoxic to normal cells than cancer cells (F), and VP16 (Etoposide phosphate) has little selectivity between normal and cancer cells (G and H).
Figure 2B:
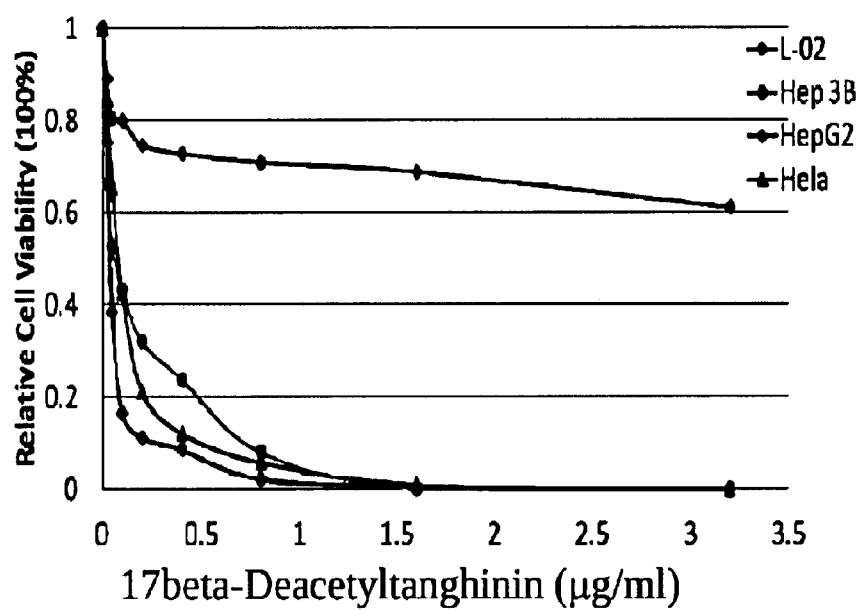
Figure 2C:
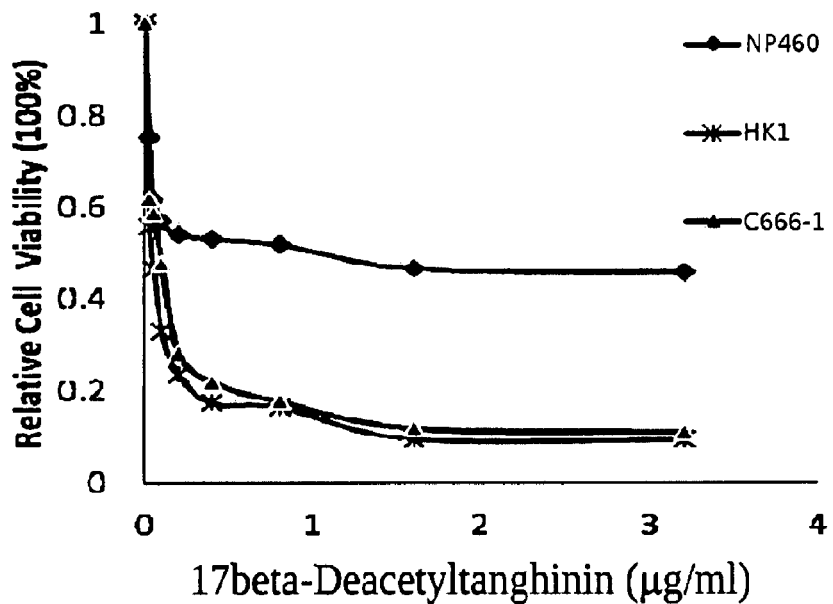
Figure 2D:
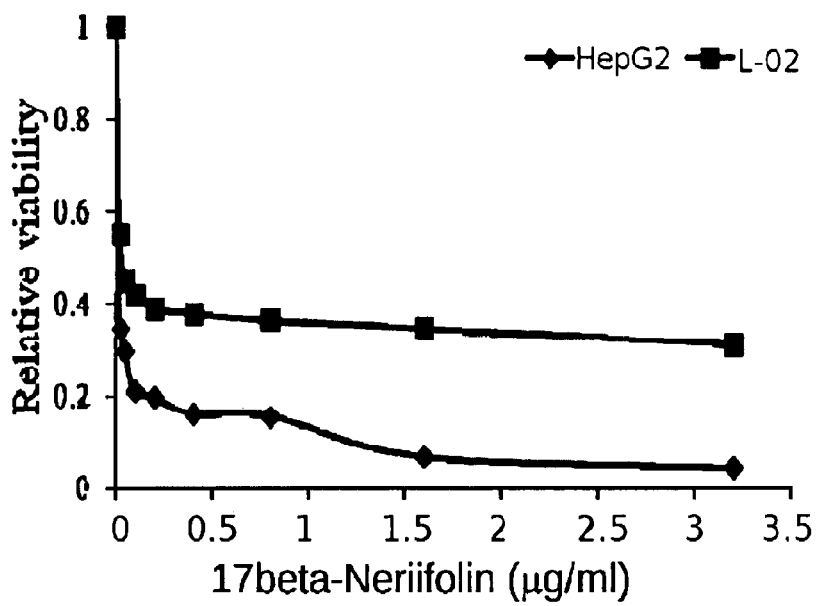
Figure 2E:
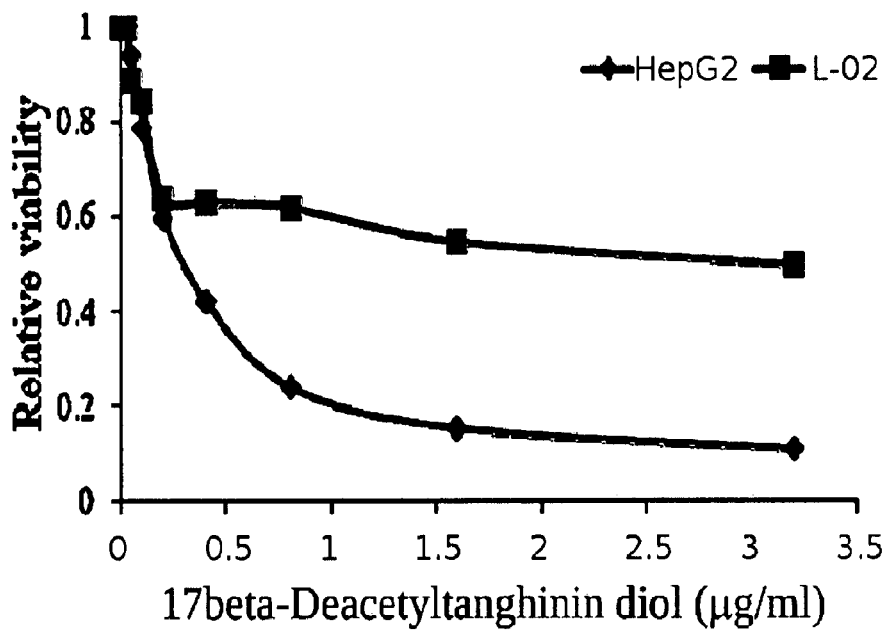

To further test 17beta-Deacetyltanghinin and to determine the IC50 values, besides L-02 and HepG2, Hep3B (another liver cancer cell line which is p53-negative), HeLa (cervical cancer cell line), HK1 and C666-1 (nasopharyngeal carcinoma) cells and a hTert-immortalized normal nasopharyngeal cell line (NP460) were treated by 17beta-Deacetyltanghinin for 48 hrs, and the relative cell vabilities were determined by WST-1 assay (FIG. 2B, C). These and other (including lung cancer, etc; data not shown) cancer cell lines were employed to demonstrate that 17beta-Deacetyltanghinin can kill a broad spectrum of cancer cells. The growth of all cancer cell lines tested was significantly inhibited by 17beta-Deacetyltanghinin. Although the IC50 values were slight different among different cancer cell lines, the average IC50 of 17beta-Deacetyltanghinin on the cancer cell lines was about 0.1 μg/ml (0.2 μM), while that for normal cells was much higher (over 4 μg/ml). Similar anticancer activity and selectivity between cancer and normal cells were obtained for some structurally related compounds, for examples, 17beta-Neriifolin (FIG. 2D), 17beta-Deacetyltanghinin diol which is a novel chemical derivative of 17beta-Deacetyltanghinin that we synthesized (with a lower anticancer activity than 17beta-Deacetyltanghinin; FIG. 2E), Bufalin, Resibufogenin and Cinobufagin (table below). On the other hand, 17alpha-Deacetyltanghinin and 17alpha-Neriifolin have little anti-proliferative activity (table below), indicating that the 17beta configuration is critical for the anti-proliferative activity of these compounds.

| Compound (0.5 ∝g/ml) | 17alpha-Deacetyltanghinin | 17alpha-Neriifolin | Bufalin | Resibufogenin | Cinobufagin |
| --- | --- | --- | --- | --- | --- |
| HepG2 cell viability (%) | 97.2 | 100 | 13.7 | 1.4 | 1.5 |
| L-02 cell viability (%) | 100 | 100 | 37.2 | 37.9 | 39.7 |

Identification of Anti-Proliferation Agents with High Specificity Between Normal and Cancer Cells Following screening of a few hundred samples that are compounds, fractions or crude extracts from plants and synthetic compounds, several candidates were identified that can inhibit human MCM proteins and DNA replication. Of these candidates, a small compound called 17beta-Deacetyltanghinin (FIG. 1), was isolated and identified after several rounds of activity-guided fractionation, purification and testing of the plant extracts, fractions and compounds. Several other compounds and a chemical derivative of 17beta-Deacetyltanghinin (7beta-Deacetyltanghinin diol) that are structurally related to 17beta-Deacetyltanghinin were also found to have similar activities as 17beta-Deacetyltanghinin (FIG. 1(3)-(8)). On the other hand, their 17alpha isomers (FIGS. 1(1) and (2)) were found to be inactive.

Figure 2F:
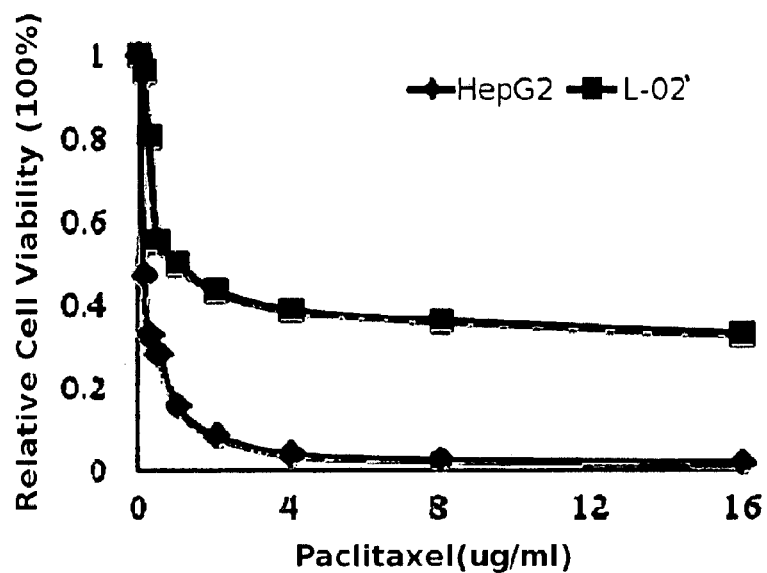
Figure 2G:
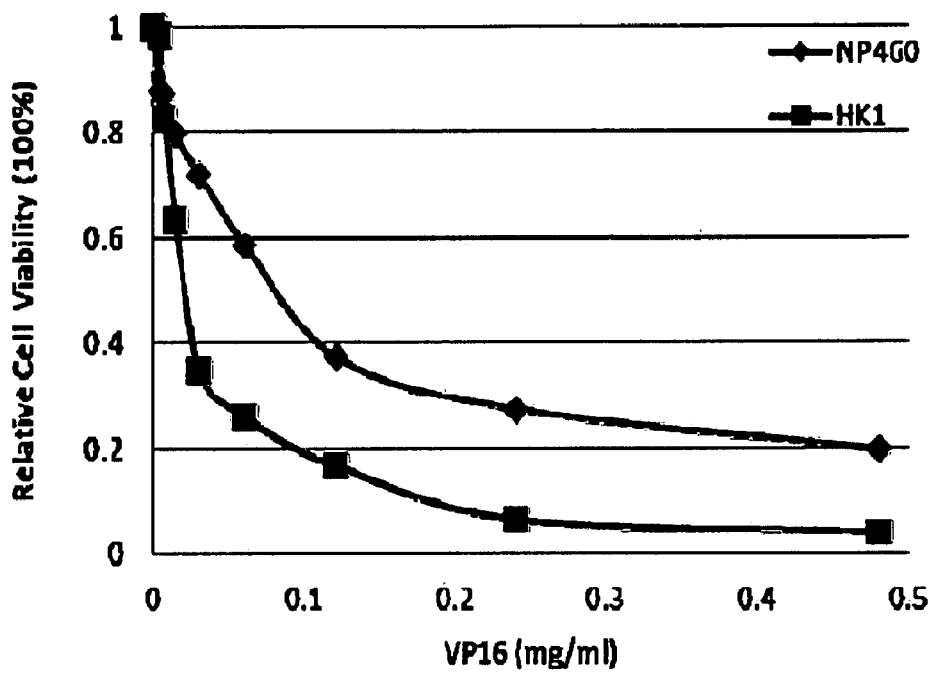
Figure 2H:
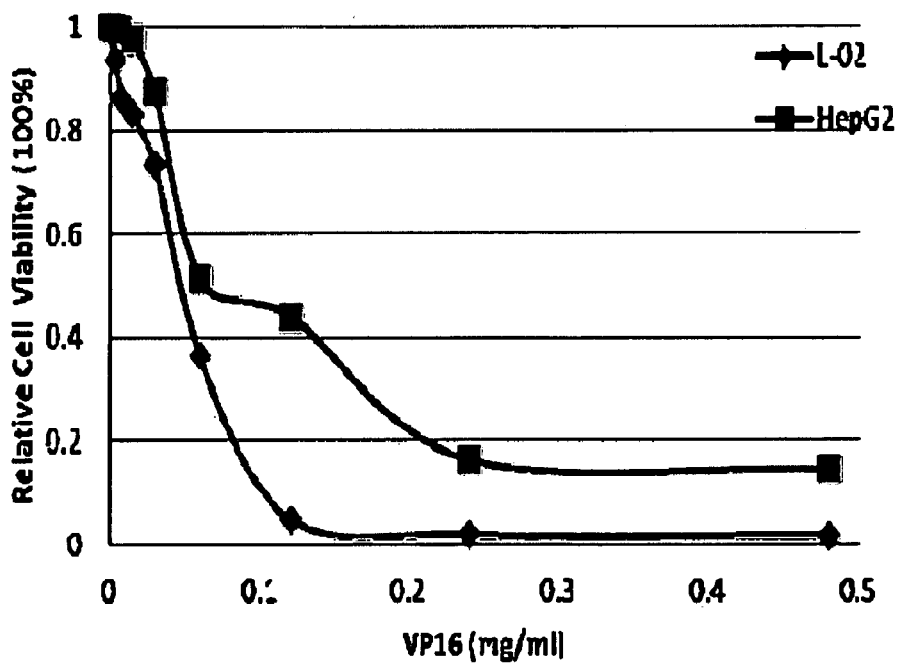

A pair of human cell lines, L-02 (normal liver cells) and HepG2 (a liver cancer cell line) was treated with 17beta-Deacetyltanghinin for 48 hrs. Direct observation of cell density and morphology under the microscopy showed that 17beta-Deacetyltanghinin can efficiently inhibit the proliferation of cancer cells (HepG2) and has a much lower activity towards normal cells (L-02) in culture (FIG. 2A). Hence 17beta-Deacetyltanghinin was identified as a highly active anti-proliferative agent with little cytotoxicity For comparison, the clinical anticancer drugs Paclitaxel (Taxol; FIG. 2F) and VP16 (Etoposide phosphate; FIG. 2G, H) did not show significant selectivity between the cancer and normal cells (they are cytotoxic to normal cells as well as cancer cells; in fact, Paclitaxel is more toxic to normal liver cells than liver cancer cells).

Figure 3A:
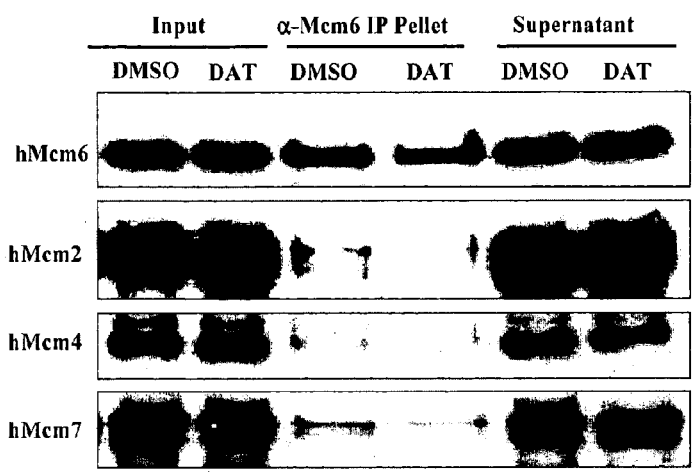
FIG. 3 shows by co-immunoprecipitation that 17beta-Deacetyltanghinin (DAT) and 17beta-Neriifolin (NRF) impair the interactions among MCM subunits, while 17beta-Deacetyltanghinin diol (Diol) has a weaker activity.
Figure 3B:
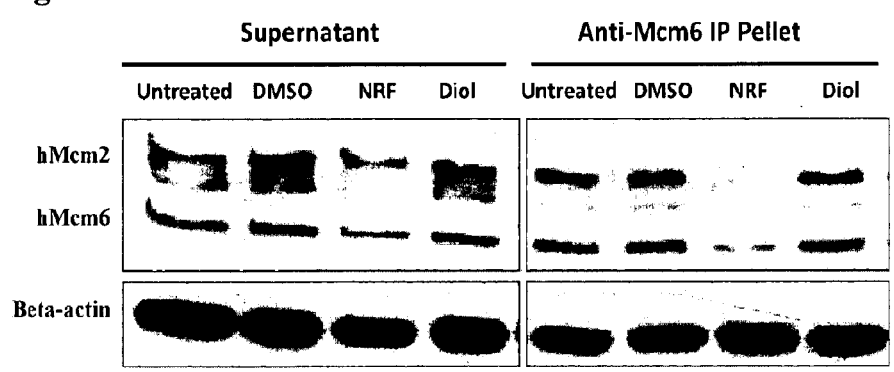

Disruption of the Formation of MCM Complex and the Nuclear Localization of MCM Proteins To test if 17beta-Deacetyltanghinin targets hMcm2 and hMcm6 proteins in human cells, possible co-immunoprecipitation (co-IP) of the two proteins was tested in human cell extracts from cells treated with 17beta-Deacetyltanghinin. In FIG. 3, asynchronous HeLa cells were treated with DMSO or 17beta-Deacetyltanghinin (DAT) (FIG. 3A), or with DMSO, 17beta-Neriifolin (NRF) or 17beta-Deacetyltanghinin diol (Diol) (FIG. 3B), and whole cell extracts were prepared and further incubated with the compound before being used for co-IP in the presence of the compound. The immunoprecipitates were then immunoblotted with anti-hMcm 6, anti-hMcm2, anti-hMcm4 and anti-hMcm7 antibodies. The results showed that 17beta-Deacetyltanghinin disrupted the interaction between hMcm2 and hMcm6 and among other MCM subunits (FIG. 3A). Similarly, 17beta-Neriifolin could also disrupt the hMcm2-hMcm6 interaction, while 17beta-Deacetyltanghinin diol showed a weaker activity (FIG. 3B).

Because pair-wise interactions among the MCM subunits are required for the MCM heterohexameric ring structure, which is essential for their import into the nucleus, disruption of the interaction between hMcm2 and hMcm6 should destroy the hexamer and result in failure of nuclear localization of MCM proteins. To test this, we employed both indirect fluorescence microscopy (immunostaining) using antibodies against the endogenous MCM proteins and direct fluorescence microscopy after transfection with plasmids to express hMcm2-GFP and hMcm6-GFP in the cells.

Figure 4A:
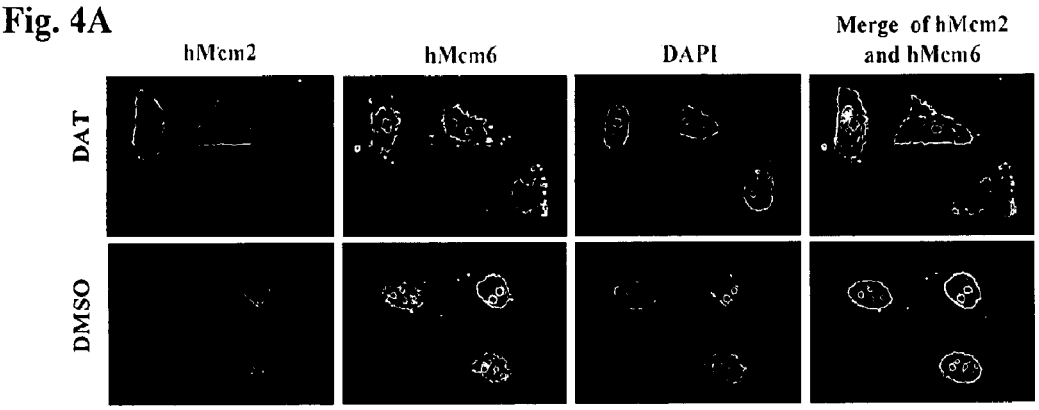
FIG. 4 presents indirect immunofluorescence microscopy data showing that 17beta-Deacetyltanghinin (DAT), 17beta-Neriifolin (NRF) and 17beta-Deacetyltanghinin diol (Diol) impair the nuclear localization of hMcm2 (h, human) and hMcm6.
Figure 4B:
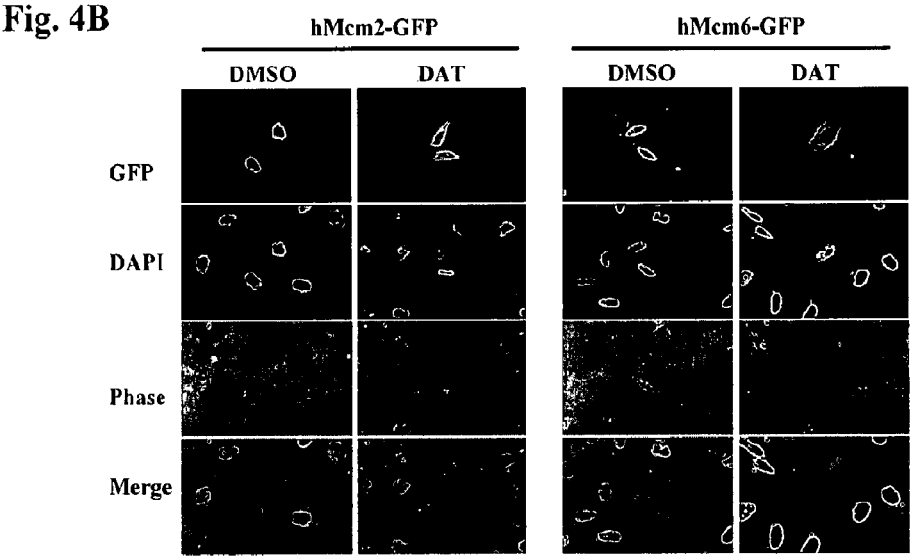

In immunostaining, HeLa cells were treated by 17beta-Deacetyltanghinin for 24 hrs, and the endogenous hMcm2 and hMcm6 were detected by specific antibodies against these proteins. The results showed that the nuclear localization of hMcm2 and hMcm6 was impaired by 17beta-Deacetyltanghinin (FIG. 4A). In direct fluorescence microscopy, HeLa cells expressing hMcm2-GFP and hMcm6-GFP were treated with 17beta-Deacetyltanghinin for 36 hrs starting at 4 hrs post-transfection with the plasmids expressing hMcm2-GFP and hMcm6-GFP. The results showed that some of the expressed hMcm2-GFP and hMcm6-GFP located in the cytoplasm, while in the untreated control cells, almost all of the expressed hMcm2-GFP and hMcm6-GFP localized in the nucleus (FIG. 4B). To exclude the possibility that the cytoplasmic localization of some MCM proteins was due to a cell cycle arrest caused by 17beta-Deacetyltanghinin, we used Mimosine to arrest cells in late G1 phase where all MCM proteins should be in the nucleus if MCM proteins are not inhibited, and we found that the nuclear localization of hMcm2 and hMcm6 were still prevented by 17beta-Deacetyltanghinin (data not shown).

Figure 4C:
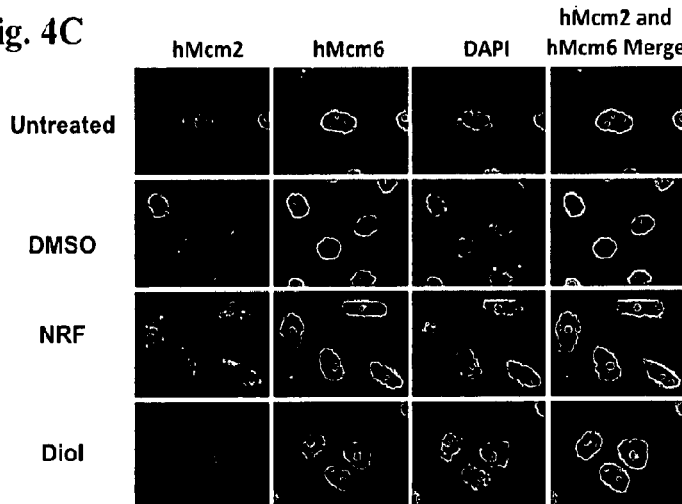

Taken together, these data indicate that 17beta-Deacetyltanghinin can specifically block the MCM nuclear localization. We also found that 17beta-Neriifolin, another compound isolated from *Cerebra manhas* and structurally related to 17beta-Deacetyltanghinin, can also disrupt the MCM nuclear localization as efficiently as 17beta-Deacetyltanghinin can, while 17beta-Deacetyltanghinin diol which is a chemical derivative of 17beta-Deacetyltanghinin has a weaker activity (FIG. 4C).

Inhibition of the Assembly of Pre-RC

Figure 5A:
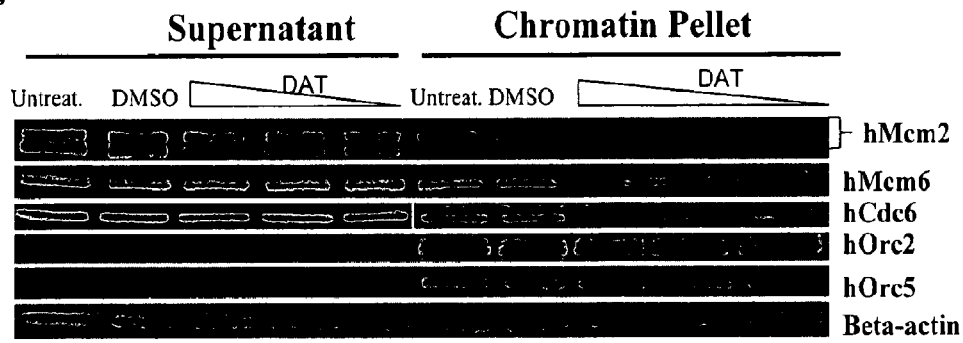
FIG. 5 presents chromatin-binding assay and flow cytometry data to show that 17beta-Deacetyltanghinin inhibits the assembly of pre-replicative complex (pre-RC) and induces apoptosis of cancer cells.
Figure 5B:
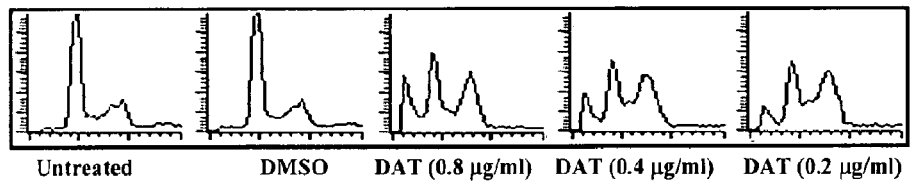

As the component of pre-RC, the MCM complex plays a central role in the licensing of DNA replication. Since 17beta-Deacetyltanghinin can disrupt the interactions of hMcm2 and hMcm6 and prevent their nuclear localization, 17beta-Deacetyltanghinin should inhibit the chromatin association of MCM proteins, indicating failure of pre-RC assembly (replication licensing). To test this, we performed chromatin binding assays to detect chromatin-associated proteins. In FIGS. 5A and B, asynchronous Hela cells were treated with 17beta-Deacetyltanghinin for 24 hrs and analyzed by the chromatin binding assay (FIG. 5A). Untreated cells (Untreat.), cells treated with the solvent DMSO, and those treated with 0.2, 0.4 or 0.8∝g/ml 17beta-Deacetyltanghinin were analyzed for pre-RC components in the chromatin and supernatant fractions by immunoblotting (FIG. 5A). Beta-actin was used as the loading control. Each cell sample was also analyzed for cell cycle distribution by flow cytometry (FIG. 5B). Experiments shown in FIGS. 5C and D were similar to those in FIGS. 5A and B, except that the cells were synchronized in M phase using Nocodazole (Noc.) and then released into fresh medium containing DMSO or 17beta-Deacetyltanghinin (DAT) as indicated.

Consistent with the prediction, both hMcm2 and hMcm6 were significantly reduced in the chromatin fractions by 17beta-Deacetyltanghinin in a dosage-dependent manner (FIG. 5A). These results suggest that pre-RC failed to assemble in the presence of 17beta-Deacetyltanghinin. Furthermore, cells underwent apoptosis as determined by flow cytometry with aliquots of the cells from the same experiment (FIG. 5B).

Figure 5C:
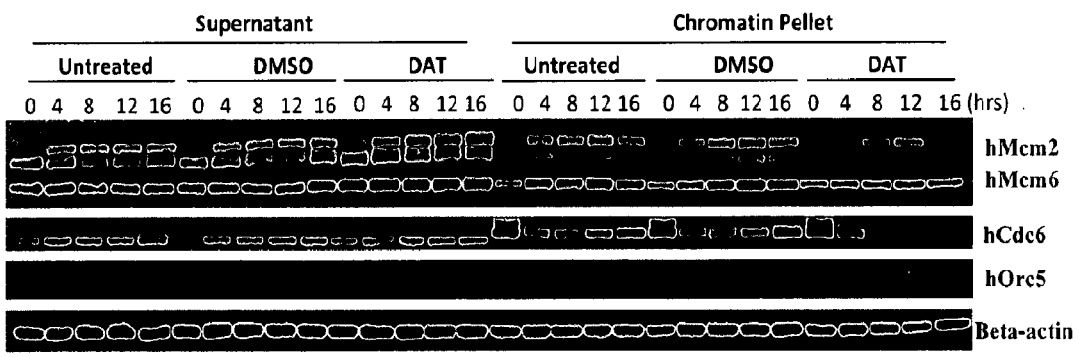
Figure 5D:
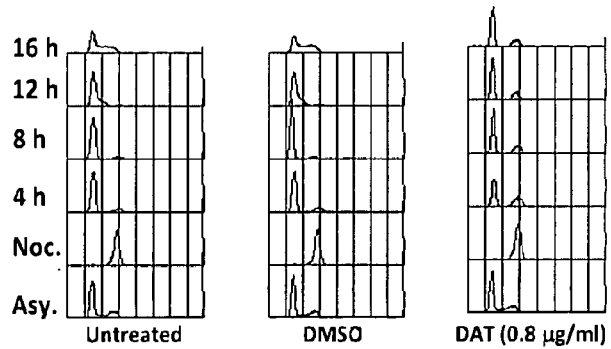

To determine the effects of 17beta-Deacetyltanghinin in synchronized cells, HeLa cells were first pre-synchronized in late G1/early S phase with thymidine and then arrested in M phase with nocadozole. The cells were then released into fresh medium in the presence of 17beta-Deacetyltanghinin. Control cells including DMSO-treated and untreated cells, could pass through M and G1 phases and enter S phase (FIG. 5D). However, 17beta-Deacetyltanghinin-treated cells only entered G1 phase, and most of the cells did not enter S phase (FIG. 5D). Immunoblotting analysis showed that MCM loading onto chromatin was largely prevented by 17beta-Deacetyltanghinin (FIG. 5C). These results indicate that 17beta-Deacetyltanghinin can prevent the assembly of pre-RC in human cells.

Inhibition of DNA Replication with Apoptosis in Cancer Cells

Figure 6A:
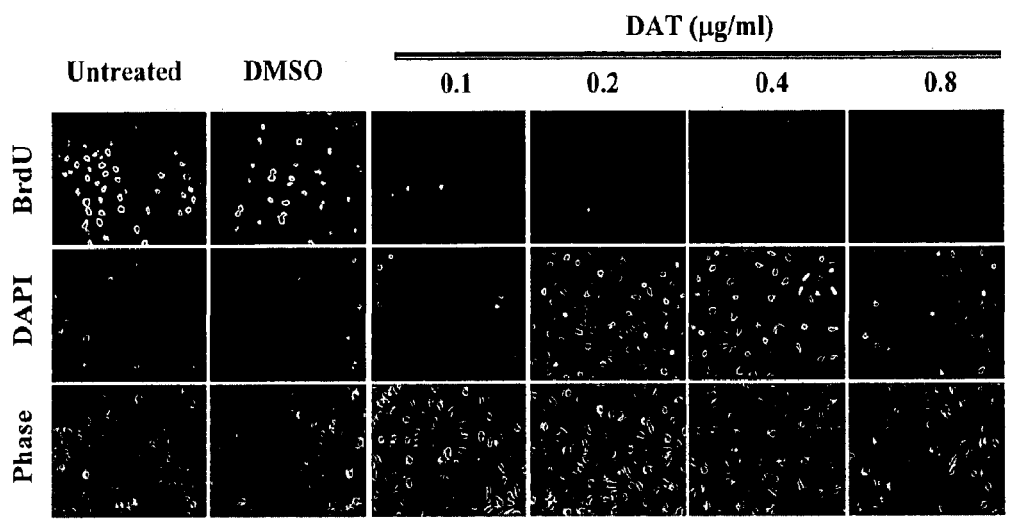
FIG. 6 shows by flow cytometry that 17beta-Deacetyltanghinin inhibits DNA replication and induces apoptosis in cancer cells.
Figure 6B:
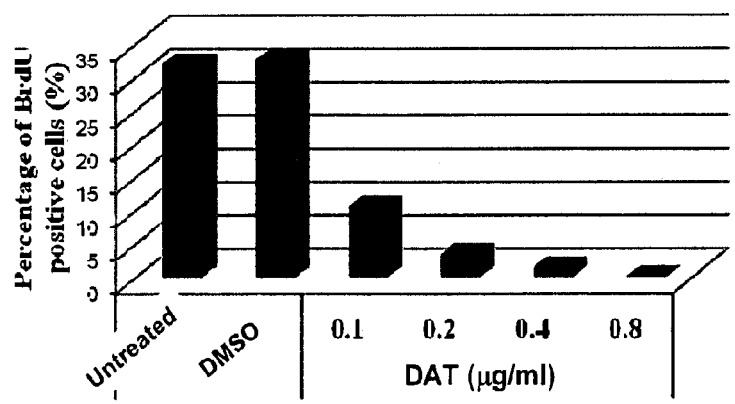

As 17beta-Deacetyltanghinin disrupts the interactions between hMcm2 and hMcm6 and inhibits the association of MCM proteins with chromatin, 17beta-Deacetyltanghinin should block DNA replication. To confirm this, we treated HeLa cells with 17beta-Deacetyltanghinin for 24 hrs and then labeled them with BrdU for 1 hr. Incorporated BrdU in the cellular DNA was detected by an anti-BrdU antibody followed by FITC-anti-mouse secondary antibodies which was visualized under the fluorescence microscope (FIG. 6A). DAPI was used to stain the nuclei (FIG. 6A), and the percentage of BrdU positive cells was quantified (FIG. 6B). Significant inhibition of DNA replication was observed in 17beta-Deacetyltanghinin-treated HeLa cells, as almost no BrdU signal was observed when 17beta-Deacetyltanghinin was above 0.2∝g/ml, while in the DMSO-treated and untreated cells, about 30% were BrdU positive as expected (FIG. 6A, B).

Figure 7A:
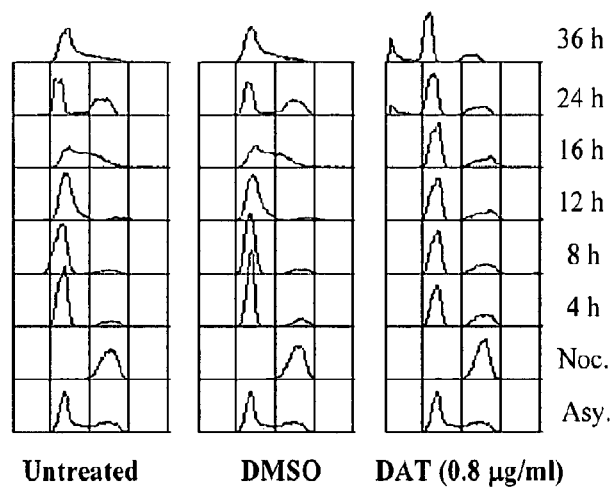
FIG. 7 presents BrdU incorporation assay data to show that 17beta-Deacetyltanghinin inhibits DNA replication.
Figure 7B:
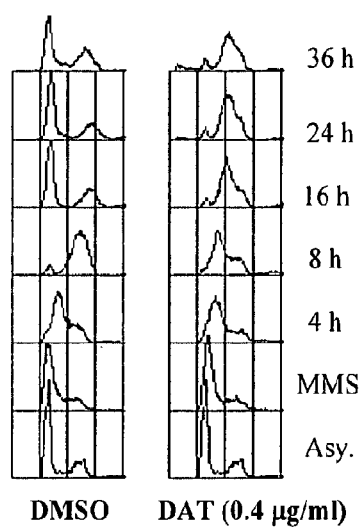
Figure 7C:
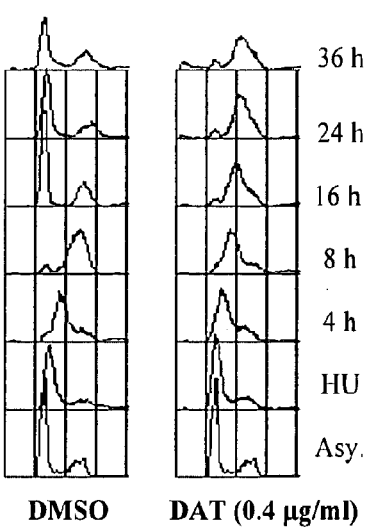

Moreover, inhibition of DNA replication and subsequent induction of apoptosis by 17beta-Deacetyltanghinin could be shown by flow cytometry. In FIG. 7. Hela cells were blocked at M phase by Nocodazole (Noc.; FIG. 7A), the G1/S transition by mimosine (MMS; FIG. 7B), or at early S phase by Hydroxyurea (HU; FIG. 7C) and then released into fresh medium in the presence of 17beta-Deacetyltanghinin (DAT). The cells at different time points after release were analyzed by follow cytometry. Ayn. means asynchronous cells. Untreated cells and cells treated with the solvent DMSO could complete M, G1 and S phases after release (FIG. 7A). Cells treated with 17beta-Deacetyltanghinin could complete mitosis but could not enter S phase after being released from the Nocodazole arrest in M phase, and started apoptosis with a longer treatment time with 17beta-Deacetyltanghinin (FIG. 7A). Similarly, cells released from the Mimosine (MMS) arrest (at the G1/S transition; FIG. 7B) or Hydroxyurea (HU) arrest (in early S phase; FIG. 7C) could not finish S phase in the presence of 17beta-Deacetyltanghinin. These results are consistent with the inhibition of the MCM functions, both in the initiation and elongation of DNA replication.

Figure 8A:
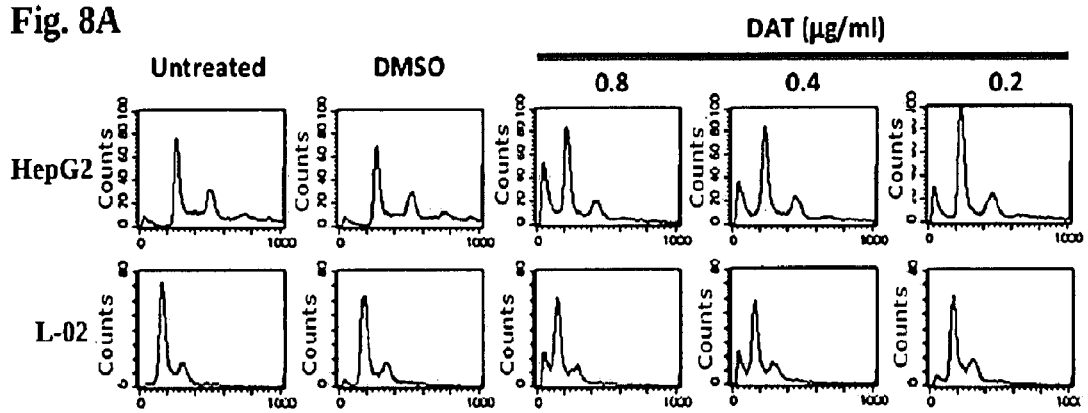
FIG. 8 presents flow cytometry and Annexin V staining data showing that 17beta-Deacetyltanghinin (DAT), 17beta-Neriifolin (NRF) and 17beta-Deacetyltanghinin diol (Diol) can induce apoptosis in cancer cells.
Figure 8B:
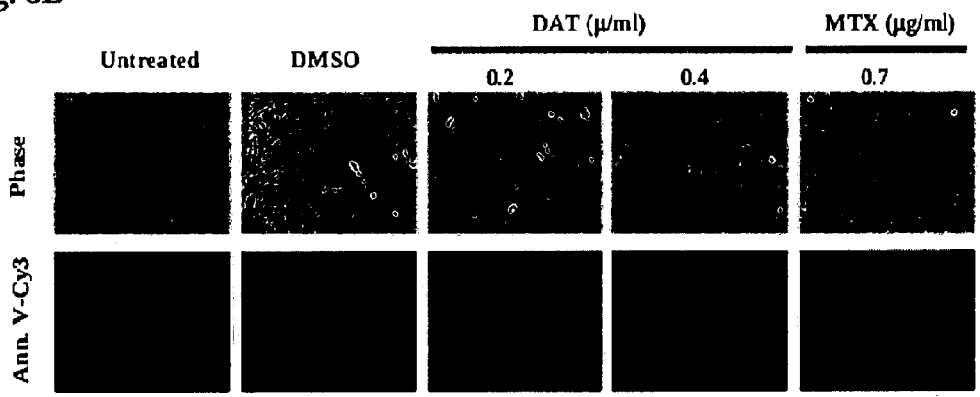

17beta-Deacetyltanghinin also induced apoptotic cell death in cancer cells, as a population of sub-G1 cancer cells, indicative of apoptosis, was detected by flow cytometry after treatment by 17beta-Deacetyltanghinin (FIGS. 5B, 7 and 8A), whereas normal L-02 cells were mostly arrested in G1 phase with reduced a G2/M population (FIG. 8A). In FIG. 8A, flow cytometry was performed to analyze the DNA contents in HepG2 and L-02 cells treated with 17beta-Deacetyltanghinin at various concentrations for 24 hrs. In FIG. 8B, Hela cells were treated with 17beta-Deacetyltanghinin for 24 hrs and labeled with Annexin V-Cy3 (Arm. Cy3) for 20 min. Mitoxantrone (MTX), a clinical anticancer drug that can induce apoptosis in cancer cells, was used as a positive control. The results show that 17beta-Deacetyltanghinin-treated cancer cells could be stained by Annexin V (FIG. 8B), supporting the notion that apoptosis was induced by 17beta-Deacetyltanghinin.

Figure 8C:
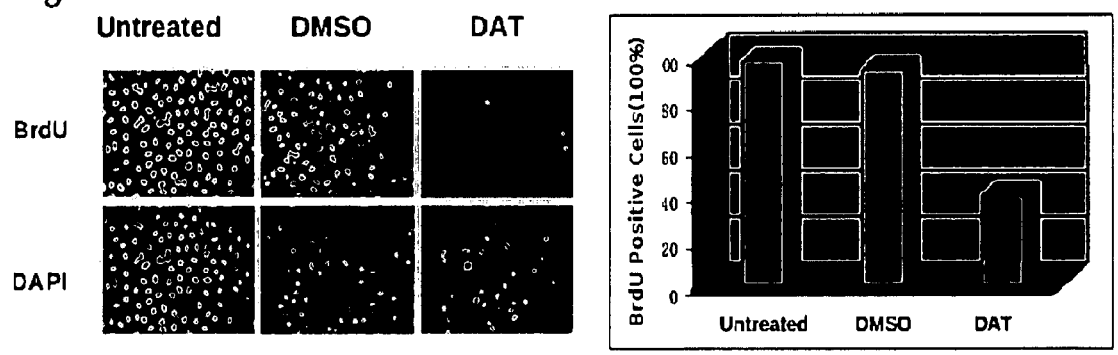
Figure 8C:
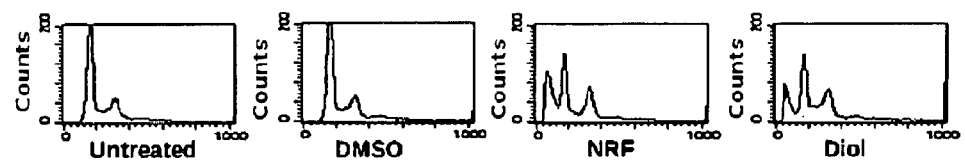

As described above, 17beta-Deacetyltanghinin inhibited DNA replication in asynchronous HeLa cells (by BrdU incorporation assay) (FIG. 6), and most of the synchronized cells released from M phase entered G1 phase but apparently did not enter S phase in the presence of 17beta-Deacetyltanghinin as judged by the flow cytometry results (FIG. 7A). Longer incubation of cancer cells with 17beta-Deacetyltanghinin could induce apoptosis as evidenced by a sub-G1 population in the flow cytometry profiles (FIG. 7A) and by Annexin V staining (FIG. 8B). To determine the cause of cell death in cancer cells treated with 17beta-Deacetyltanghinin, we arrested HeLa cells at the G1/S transition with Mimosine and then added 17beta-Deacetyltanghinin into the medium to pre-treat the cells for 12 hrs. The cells were then released from the Mimosine block in the presence of 17beta-Deacetyltanghinin, harvested at different time points after release, and analyzed by flow cytometry and BrdU incorporation assays. BrdU incorporation results showed that ~40% of the cells treated with 17beta-Deacetyltanghinin were BrdU positive, compared to ~100% BrdU-positive untreated cells and cells treated DMSO; however, the BrdU signal intensities in the 17beta-Deacetyltanghinin-treated cells were much lower than those in untreated cells and DMSO-treated cells (FIG. 8C), indicating that at least some 17beta-Deacetyltanghinin-treated cells underwent a low degree of DNA replication, which was attributable to incomplete inhibition of the MCM complex and hence a low degree of activation of some replication origins and limited elongation of DNA replication in 17beta-Deacetyltanghinin-treated cells. As such, the abortive partial duplication of the genome most likely caused DNA damage, leading to apoptosis.

In addition to 17beta-Deacetyltanghinin, a number of structurally related compounds, for example, 17beta-Neriifolin and 17beta-Deacetyltanghinin diol were also found to be able to induce apoptosis of cancer cells as indicated by the sub-G1 population of cells in flow cytometry analysis (FIG. 8D).

Figure 9:
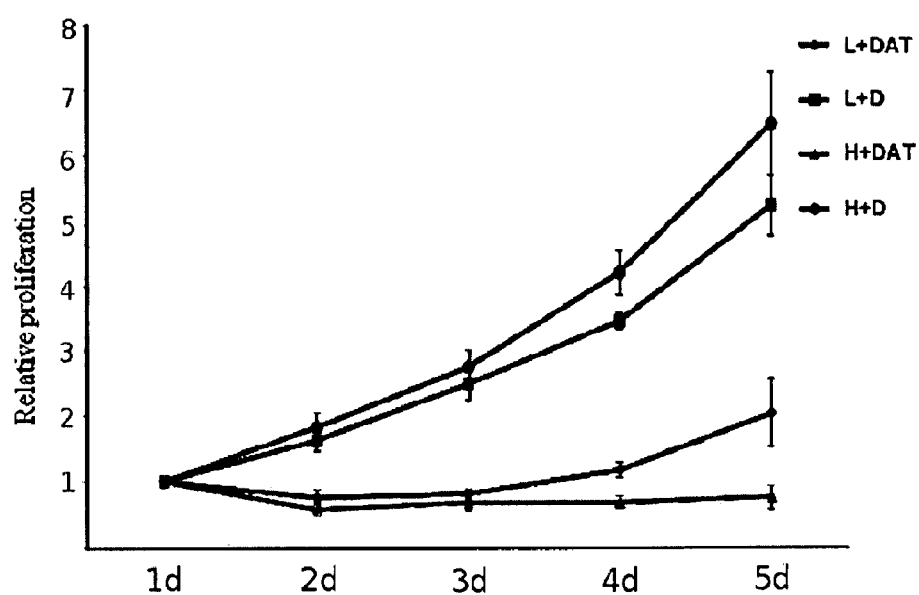
FIG. 9 shows that normal cells, but not cancer cells, are capable of resuming growth after removal of 17beta-Deacetyltanghinin as measured by WST-1 assay.

Further Testing of the Specificity of the Anti-Proliferation Compounds Towards Cancerous Cells Data in FIGS. 2 and 8A indicate that the anti-proliferation compounds of this invention can specifically kill cancer cells with little cytotoxicity towards normal cells. To test if normal and/or cancer cells could resume cell growth after removal of 17beta-Deacetyltanghinin, L-02 (normal liver) cells and HepG2 (liver cancer) cells were incubated with 17beta-Deacetyltanghinin or DMSO for one day, 17beta-Deacetyltanghinin or DMSO was then removed, and the cells were further incubated with fresh growth medium for three days. Viable cell numbers were monitored daily by WST-1 assay. In FIG. 9, L+DAT refers to L-02 cells treated with 17beta-Deacetyltanghinin; L+D represents L-02 cells treated with DMSO; H+DAT refers to HepG2 cells treated with 17beta-Deacetyltanghinin; and H+D represents HepG2 cells treated with DMSO before being released into fresh medium. The results showed that normal cells, but not cancer cells, resumed growth after removal of 17beta-Deacetyltanghinin (FIG. 9), consistent with our findings that the majority of normal cells stayed in G1 phase when they were treated with 17beta-Deacetyltanghinin, whereas cancer cells entered an abortive S phase and died under the same treatment (FIG. 8A).

In Vivo Anticancer Activity in the Nude Mice Xenograft Model

Figure 10A:
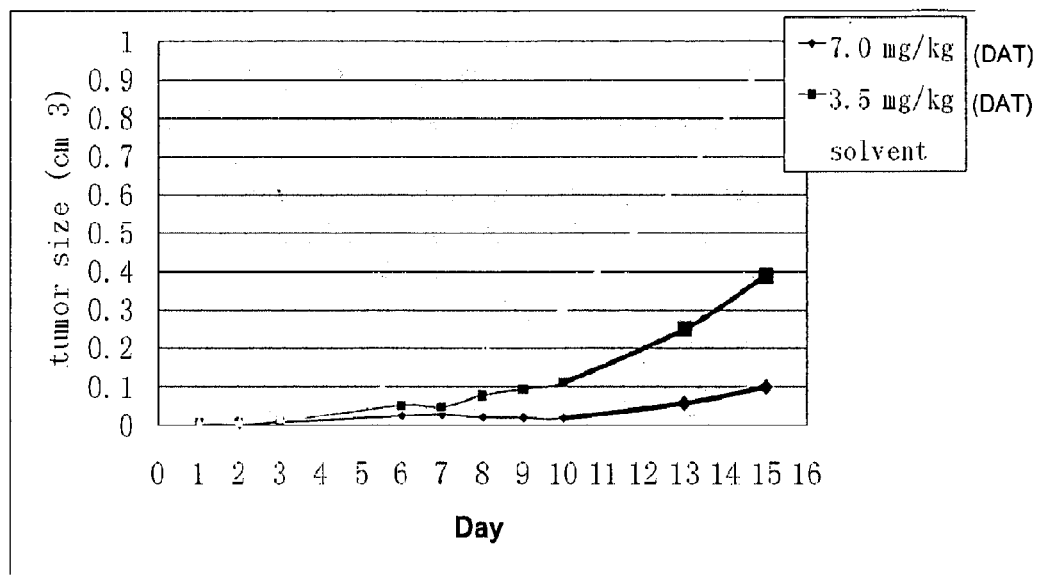
FIG. 10 shows the in vivo antitumor activity of 17beta-Deacetyltanghinin in nude mice xenograft models.

In vivo anticancer activity tests were carried out in the nude mice xenograft model by inoculating nude mice with HeLa cells in both the left and right flanks. After random grouping, nude mice were treated intraperitoneally with 17beta-Deacetyltanghinin or the solvent (30% of propylene glycol in PBS). In the first test, 3 days after tumor inoculation when small tumors started to form, two groups of nude mice were treated on days 1-3 and 6-10 with 3.5 and 7.0 mg-drug/kg-body weight of 17beta-Deacetyltanghinin respectively, and another group of control mice were treated with the same volume of the solvent (FIG. 10A). In FIG. 10A, the tumor volume data represented by the small-size data point symbol linked with thin lines were obtained on the days when both measurement of tumor size and drug injections were performed, and the tumor volume data represented by the large-size data point symbol linked with thick lines were obtained on the days without drug injection. Each tumor size was average of ten tumors in five mice in each group. The results showed that 17beta-Deacetyltanghinin significantly suppressed tumors growth by 90% at the high dose (7.0 mg/kg) and 70% at the low dose (3.5 mg/kg). In fact, at the high dose, for the last 5 continuous injections of 17beta-Deacetyltanghinin, tumors size even decreased, suggesting that 17beta-Deacetyltanghinin had induced the death of tumor cells in the mice.

Comparative Study with Taxol and In Vivo Toxicity Assessments

Figure 10B:
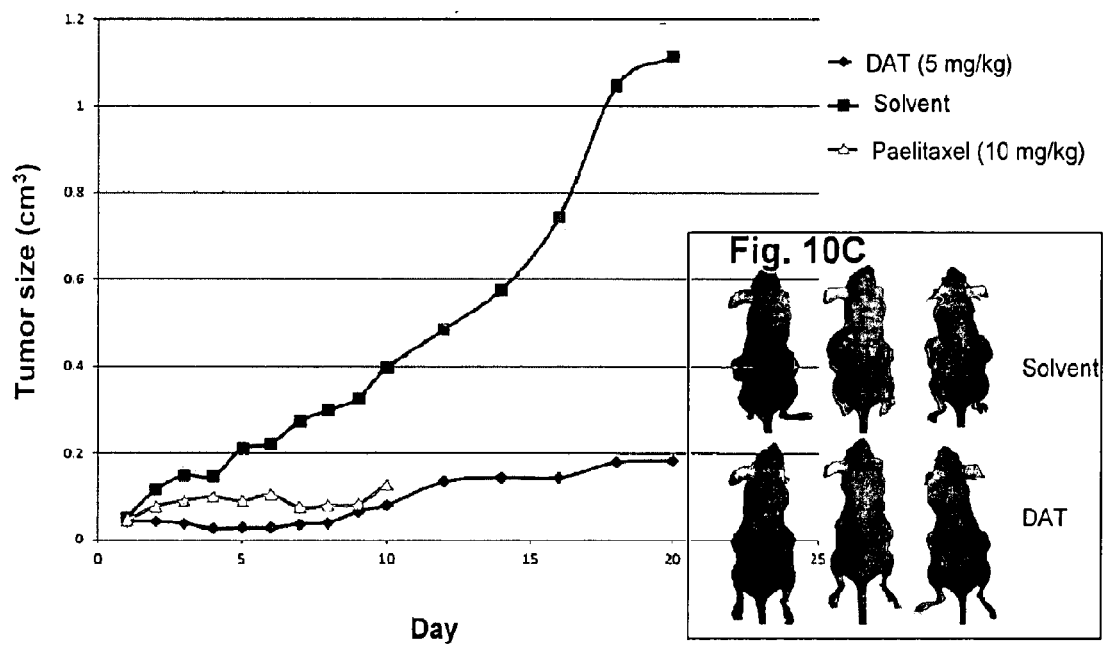

A further set of animal experiments was then conducted with a longer period of time, in which fifteen drug injections at 5.0 mg/kg were performed one week after tumor inoculation when the tumor size reached 0.05-0.1 $cm^3$. In FIG. 10B, drug injections and tumor size measurements were performed on the days represented by the data points, and the photographs in FIG. 10C were taken on day 20. The results showed that tumor growth was again significantly suppressed; tumors in the mice treated with 17beta-Deacetyltanghinin were over 80% smaller than those in the solvent-treated control mice (FIG. 10B, C). For comparison, Paclitaxel (Taxol) at 10 mg/kg per injection showed much less antitumor activities than 17beta-Deacetyltanghinin in the first 10 days, and the mice died on day 10 because of the toxicity of Taxol (FIG. 10B).

Figure 11A:
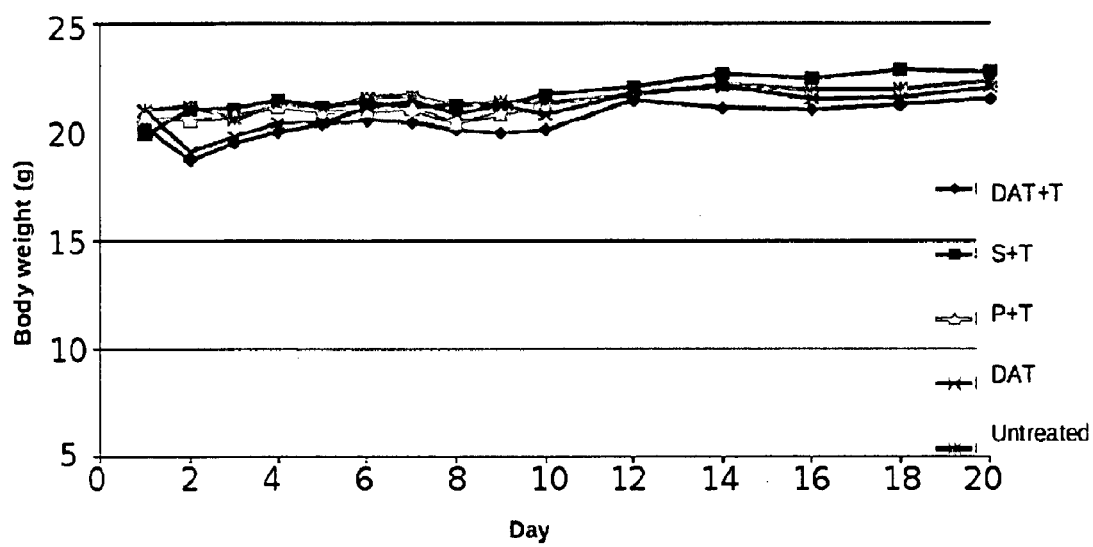
FIG. 11 shows that 17beta-Deacetyltanghinin has no obvious toxicity in nude mice, which were subjected to the experiment shown in FIG. 10.
Figure 11B:
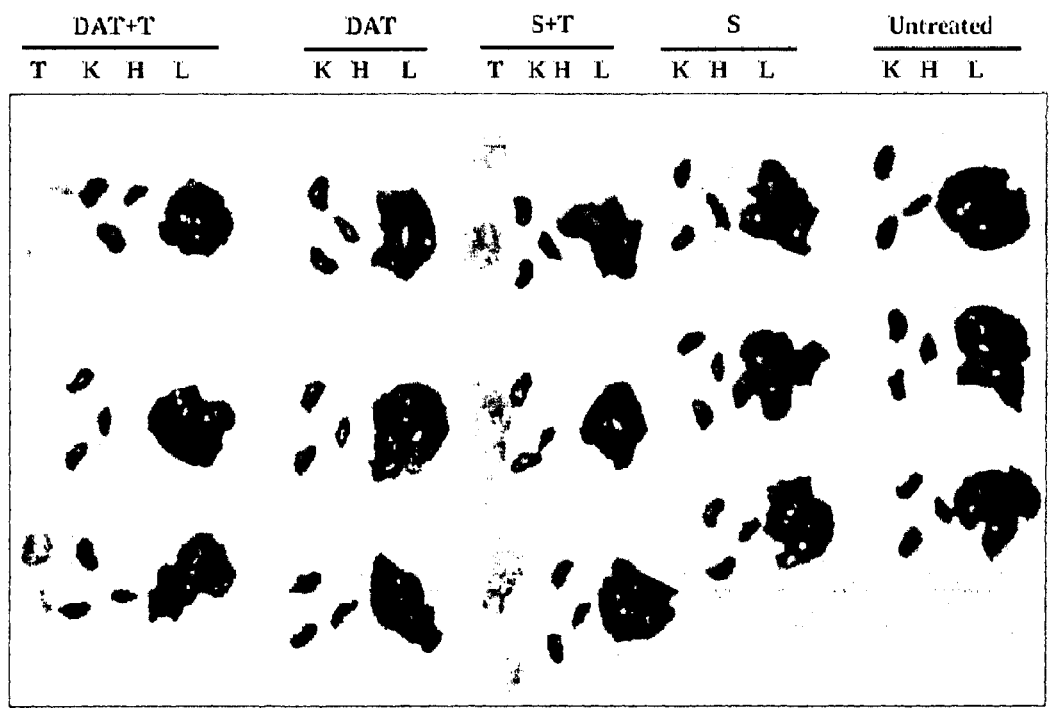
Figure 11:
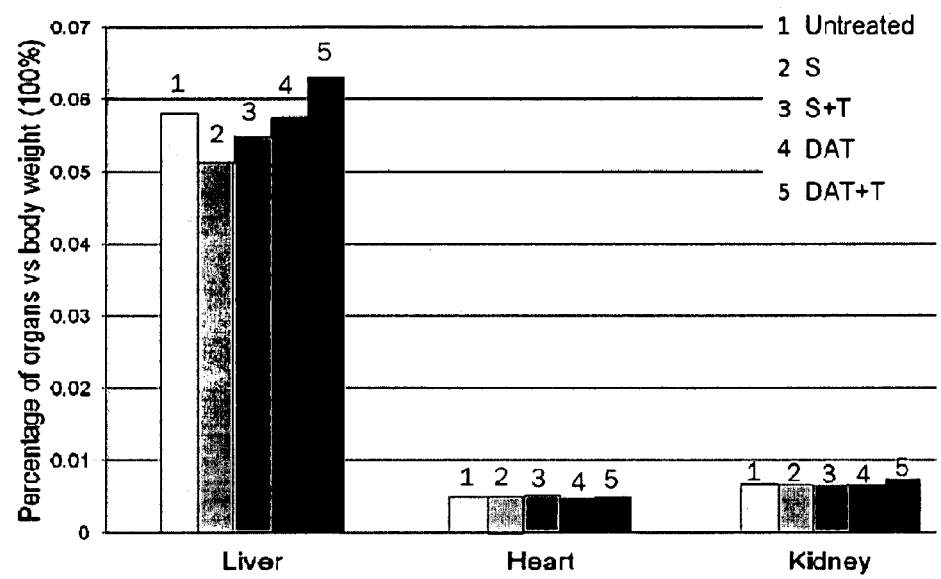
Figure 11:
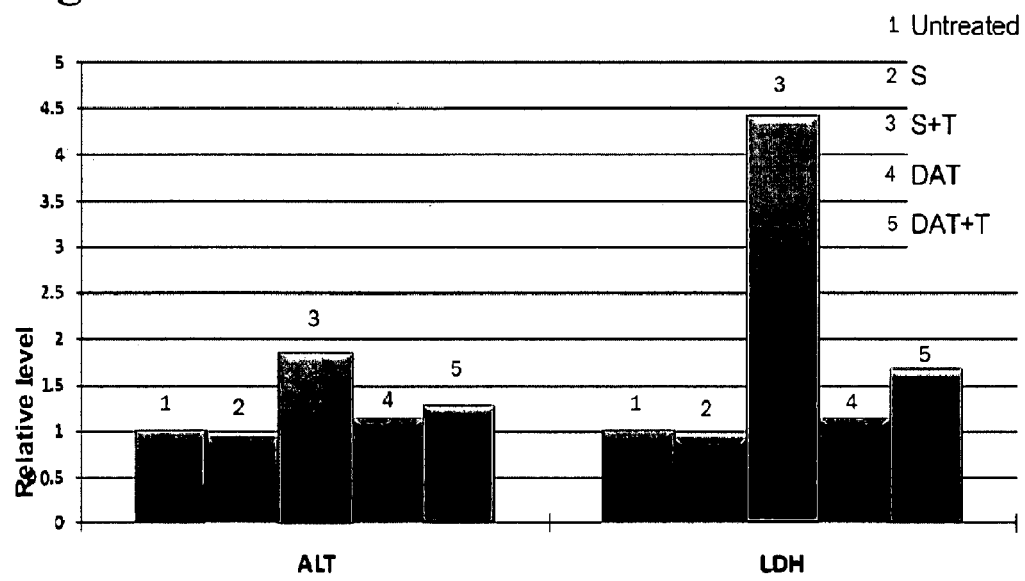

At the end of the drug treatment as described in FIG. 10B, no obvious weight loss was observed in the nude mice after intraperitoneal administration with 5.0 mg/kg of 17beta-Deacetyltanghinin for 20 days (FIG. 11A). In FIG. 11, S refers to solvent-treated mice without tumor inoculation; S+T represents solvent-treated mice with tumor inoculation; DAT refers to 17beta-Deacetyltanghinin-treated mice without tumor inoculation; DAT+T represents 17beta-Deacetyltanghinin-treated mice with tumor inoculation; and P+T refers to Paelitaxel-treated mice with tumor inoculation. Three out of the five mice with intermediate tumor size in each group were selected for physiological parameters examination. The tumors (T) and internal organs including liver (L), heart (H) and kidney (K) were dissected from each mouse. The size of the tumors (FIG. 11B) were consistent with the tumor volume measurements presented in FIG. 10B. All organs looked normal, e.g., neither intumescence nor abnormal color was observed (FIG. 11B), and the organ weights relative to body weights were not significantly changed (FIG. 11C).

Furthermore, blood from each mouse was also collected for the tests of the ALT (alanine aminotransferase) and LDH (Lactate dehydrogenase) activities. The ATL level reveals liver damage while the LDH level generally reflects damages to any tissues. The results of both tests were represented as the values of differently treated mice relative to the untreated ones. As shown in FIG. 11D, 17beta-Deacetyltanghinin did not induce significant increase of the blood ATL or LDH level. Taken together, these data strongly suggest that 17beta-Deacetyltanghinin has significant anti-tumor activity with little toxicity in mice.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of treating cancer in a patient, comprising administering to the patient a therapeutically effective amount of a pharmaceutical composition comprising an anticancer agent selected for its inhibitory effect on the human MCM complex in cancerous cells, wherein said selected anticancer agent comprises 17-beta-Deacetyltanghinin diol.

2. The method according to claim 1, wherein said anticancer agent is selected further for its ability of causing cancerous cells into an abortive S phase and normal cells substantially to arrest in G1 phase.

3. The method according to claim 2, wherein said inhibitory effect is effected by disrupting a formation of a functional MCM complex from MCM subunits.

4. The method according to claim 3, wherein said functional MCM complex is a hetero-hexameric ring structure capable of moving into the nucleus and is necessary for DNA replication.

5. The method according to claim 3, wherein selected anticancer agent disrupts the formation of the functional MCM complex by interfering an interaction between hMcm2 and hMcm6.

6. The method according to claim 1, wherein said anticancer agent further comprises 17-beta-Neriifolin.

7. A method of treating cancer in a patient, comprising administering to the patient a therapeutically effective amount of a pharmaceutical composition comprising an anticancer agent selected for its inhibitory effect on the human MCM complex in cancerous cells, wherein said selected anticancer agent is 17-beta-Deacetyltanghinin, and said cancer is cervical cancer, nasopharyngeal cancer, liver cancer, prostate cancer, colon cancer, ovary cancer, acute myelocytic leukemia, chronic lymphocytic leukemia, Non-Hodgkin's disease lymphoma, Hodgkin's disease lymphoma, acute lymphocytic leukemia, pancreatic cancer, stomach cancer, skin cancer, bladder cancer, esophageal cancer, follicular lymphoma, or non-small cell lung cancer.

8. A method of treating cancer in a patient, comprising administering to the patient a therapeutically effective amount of to inhibit the human MCM complex in cancerous cells, wherein said selected anticancer agent consists of 17-beta-Neriifolin, and said cancer is cervical cancer, stomach cancer, bladder cancer, or esophageal cancer.

* * * * *